United States Patent
Lai

(10) Patent No.: US 6,469,057 B1
(45) Date of Patent: *Oct. 22, 2002

(54) METHODS FOR IN VIVO REDUCTION OF FREE RADICAL LEVELS AND COMPOSITIONS USEFUL THEREFOR

(75) Inventor: Ching-San Lai, Encinitas, CA (US)

(73) Assignee: MCW Research Foundation, Inc., Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/672,140

(22) Filed: Sep. 27, 2000

Related U.S. Application Data

(63) Continuation-in-part of application No. 08/863,059, filed on May 23, 1997, now abandoned, which is a continuation-in-part of application No. 08/767,125, filed on Dec. 9, 1996, now Pat. No. 5,847,004, which is a continuation-in-part of application No. 08/554,196, filed on Nov. 6, 1995, now Pat. No. 5,741,815, which is a continuation-in-part of application No. 08/459,518, filed on Jun. 2, 1995, now Pat. No. 5,756,540.

(51) Int. Cl.$^7$ .................. A61K 31/28; A61K 31/325
(52) U.S. Cl. .................. 514/492; 514/491; 514/502
(58) Field of Search ................. 514/492, 491, 514/502

(56) References Cited

U.S. PATENT DOCUMENTS 5,741,815 A * 4/1998 Lai .............................. 514/492
5,756,540 A * 5/1998 Lai .............................. 514/492

* cited by examiner

Primary Examiner—Charanjit S. Aulakh
(74) Attorney, Agent, or Firm—Stephen E. Reiter; Foley & Lardner

(57) ABSTRACT

In accordance with the present invention, there are provided methods for the in vivo reduction of free radical levels in mammalian subjects in need thereof. In contrast to the inhibitory approach described in the prior art (i.e., wherein the function of the species responsible for free radical production is inhibited), the present invention employs a scavenging approach whereby overproduced free radical is bound in vivo to a suitable free radical scavenger. An exemplary free radical scavenger contemplated for use in the practice of the present invention is a dithiocarbamate-ferrous iron complex. This complex binds to free radicals, forming a stable, water-soluble free radical-containing complex. When administered to a subject afflicted with a disorder associated with free radical overproduction, the water-soluble free radical-containing complex is produced and then filtered through the kidneys, concentrated in the urine, and eventually excreted by the subject, thereby reducing in vivo free radical levels.

42 Claims, 6 Drawing Sheets

10 G

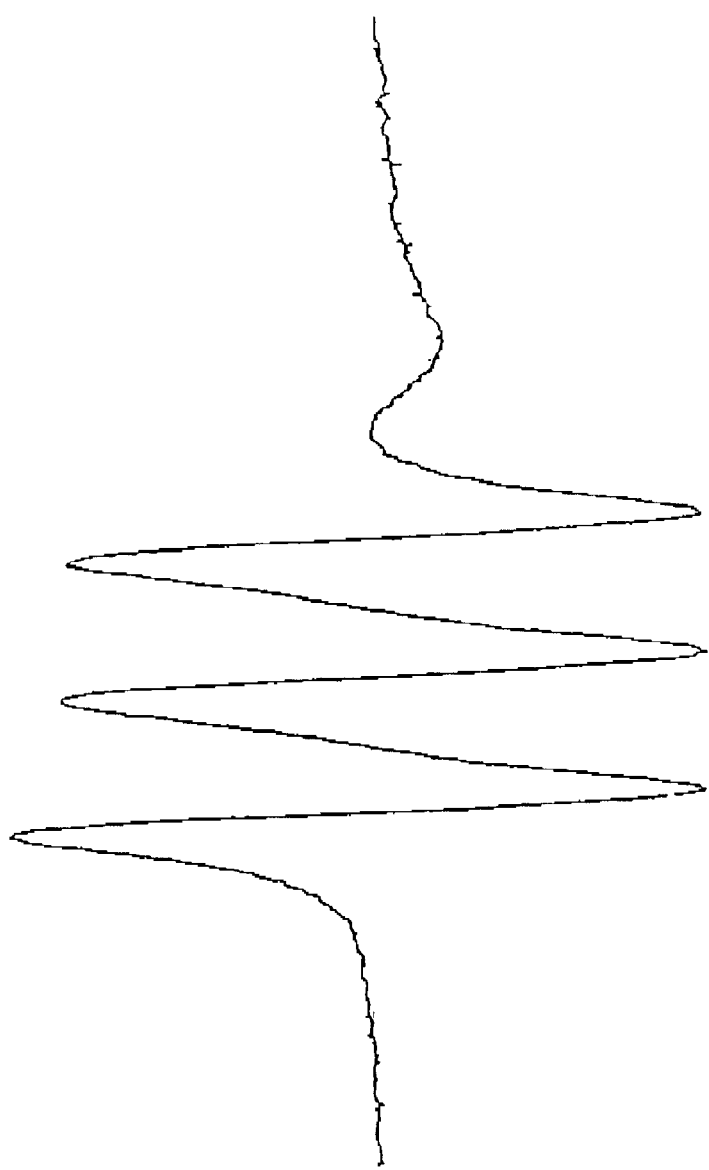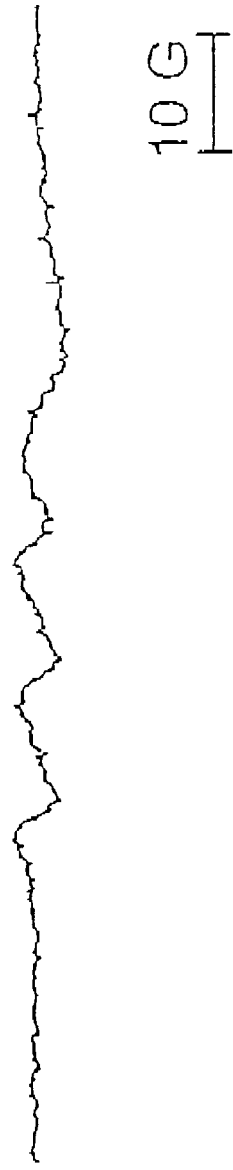
FIGURE 5A
FIGURE 5B

10 G

US 6,469,057 B1

METHODS FOR IN VIVO REDUCTION OF FREE RADICAL LEVELS AND COMPOSITIONS USEFUL THEREFOR

RELATED APPLICATIONS

This application is a continuation-in-part of U.S. application Ser. No. 08/863,059, filed May 23, 1997, abandoned, which is a continuation-in-part of U.S. Ser. No. 08/767,125, filed on Dec. 9, 1996 now U.S. Pat. No. 5,847,004, issued Dec. 8, 1998, which is a continuation-in-part of U.S. Ser. No. 08/554,196 filed on Nov. 6, 1995 now U.S. Pat. No. 5,741,815, issued Apr. 21, 1998, which is, in turn, a continuation-in-part of U.S. Ser. No. 08/459,518, filed on Jun. 2, 1995 now U.S. Pat. No. 5,756,540, issued May 26, 1998, the entire contents of each of which are hereby incorporated by reference herein.

This invention was made with Government support under grant GM-35719, awarded by the National Institutes of Health. The Government has certain lights in the invention.

FIELD OF THE INVENTION

The present invention relates to methods for reducing free radical levels in mammals. In a particular aspect, the present invention relates to methods for treating free radical overproduction in mammals by administration of physiologically active dithiocarbamate compounds which non-covalently bind free radicals in hosts afflicted with a variety of disorders. In a further aspect, the present invention relates to methods for treating free radical overproduction in mammals by administration of physiologically compatible dithiocarbamate-containing free radical scavengers in hosts afflicted with a variety of disorders.

BACKGROUND OF THE INVENTION

Free-radicals are chemical species having one or more unpaired electrons. Such species are formed by a variety of processes including photolysis, thermal homolysis, and radical-forming redox reactions. Nitric oxide, for example, is formed by the enzymatic oxidation of:L-arginine to citrulline via the action of nitric oxide synthase. Radical formation can also proceed via a variety of chain reactions. For example, the reduction of molecular oxygen by one electron gives rise to superoxide radical anion. Addition of a second electron to superoxide produces peroxide ion, which lacks an unpaired electron and is thus not a radical. Peroxide ion, however, will almost immediately protonate hydrogen peroxide at physiological pH, yielding a molecule of water and a molecule of hydroxyl radical, the strongest known oxidant produced in biological systems.

Free radicals are produced in conjunction with a variety of normal biological processes, such as mitochondrial electron transfer, and can play important roles in normal physiology. Because of their high reactivity, overproduction or inappropriate production of free radical species can be detrimental. For example, generation of superoxide radical is associated with reperfusion injury following stroke or acute myocardial infarction (McCord, N. Engl. J. Med. 312:159–163, 1985), and hydroxyl radicals are associated with a variety of neurodegenerative disorders (Evans, Br. Med. Bull. 49:577–587, 1993).

The majority of treatments for excess free radical production available to date involve the use of enzymatic inhibitors to reduce radical production, or the use of protein-based antioxidants, such as superoxide dismutase, to neutralize and reduce the potential cytotoxic effects of free radicals. Both of these approaches have proved unsatisfactory, in particular because by the time a patient presents with symptoms and can be treated, substantial amounts of free radicals have already been produced.

The use of dithiocarbamates in medical applications has been proposed in. limited circumstances. For example, dithiocarbamates have been used clinically for treatment of heavy metal intoxication. See, for example, F. W. Sunderman in *Ann Clin Lab Sci* 9(1):1–10 (1979); and M. M. Jones et al., in *Fundamental Appl. Toxicology* 19:432–437 (1992). Dithiocarbamates have also been used to alleviate renal toxicity associated with cis-platinum chemotherapy. See, for example, R. Qazi et al., in *J Natl Cancer Inst* 80:1486–1488 (1988); and D. R. Gandara et al., in *J Clin Oncol* 13:490–496 (1995). A specific dithiocarbamate, diethyldithiocarbamate, has been shown to inhibit HIV progression. This has led to clinical trials for the use of this compound in the treatment of AIDS patient populations (see, for example, E. Reisinger et al., in *Lancet* 335:679–682 (1990)).

Diethyldithiocarbamate has also been the subject of a limited study on potential in vitro antioxidants. See Ames, et. al. *Free Rad. Res.*, 24(6), p. 461, (1996). This study addresses only the in vitro reaction chemistry of diethyldithiocarbamate with HOCl and hydroxyl radical, but is conspicuously silent on the use of this or any other dithiocarbamate for the in vivo reduction of free radical levels.

Dithiocarbamates such as pyrrolidine dithiocarbamate have been determined to be potent inhibitors of nuclear factor kappa B (NFKB) in intact cells (see, for example, R. Schreck et al., in *J Exp Med* 175:1181–1194 (1992). In addition, NFKB has also been shown to up-regulate the expression of cell adhesive molecules, including the vascular cell adhesive molecule-1 (VCAM-1; see, for, example, M. F. Iademarco et al., in *J Biol Chem* 267:16323–16329 (1992)). Interestingly, in view of these known effects of dithiocarbamates on NFKB, Medford et al. propose the use of dithiocarbamates to treat cardiovascular diseases mediated by VCAM-1, through the inhibition of the NFKB pathway (see U.S. Pat. No. 5,380,747).

Accordingly, there is still a need in the art for processes to reduce free radical levels in vivo. In addition, there is also a need in the art for reagents useful for treatment of the cytotoxic effects associated with free radical overproduction, such as occurs in reperfusion injury, neurodegenerative disorders, and a variety of other diseases and conditions. The present invention addresses these and related needs.

BRIEF DESCRIPTION OF THE INVENTION

In accordance with the present invention, methods have been developed for the in vivo reduction of free radical levels in subjects in need thereof. In contrast to treatment approaches described in the prior art, the present invention employs a scavenging approach whereby overproduced free radical is bound in vivo to a suitable free radical scavenger. The resulting complex renders the free radical harmless, and is eventually excreted in the urine of the host. Further in accordance with the present invention, there have been developed compositions and formulations useful for carrying out the above-described methods.

An exemplary free radical scavenger contemplated for use in the practice of the present invention is a dithiocarbamate-ferrous iron complex. This complex binds non-covalently to free radicals, forming a stable, water-soluble dithiocarbamate-iron-free radical complex.

The present invention relates to methods for reducing in vivo levels of free radicals as a means of treating subjects afflicted with inflammatory and/or infectious disease, reperfusion injury, neurodegerative disorders, and the like. Suitable free radical scavengers are administered to a host in need of such treatment; these scavengers interact with in vivo produced free radical, forming a stable non-covalently bound free radical-containing complex. Whereas un-complexed free radicals are highly reactive chemical species, non-covalently bound free radical-containing complexes are not. The free radical-containing complex is then filtered through the kidneys, concentrated in the urine, and eventually excreted by the subject, thereby reducing in vivo free radical levels.

BRIEF DESCRIPTION OF THE FIGURES

FIG. 1A presents results where [(MGD)$_2$/Fe] complex above was injected.

FIG. 1B presents results where [(MGD)$_2$/Fe] complex and NMMA were injected.

FIG. 1C presents results where [(MGD)$_2$/Fe] complex and dexamethasone were injected.

FIG. 2A presents results where [(MGD)$_2$/Fe] complex and 10 mg of $^{15}$N-arginine were injected.

FIG. 2B presents results where [(MGD)$_2$/Fe] complex and 5 mg of $^{15}$N-arginine were injected.

FIG. 3A exhibits a characteristic two-line spectrum of [(MGD)$_2$/Fe-$^{15}$NO] complex (●). The dotted line spectrum of the [(MGD)$_2$/Fe—$^{14}$NO] complex in A (○) was obtained when $^{15}$N-arginine was omitted from the above injection solutions.

FIG. 3B illustrates the ex vivo X-band EPR spectrum of whole blood obtained from the $^{15}$N-arginine treated mice.

FIG. 4A presents spectra obtained from liver tissue. The two-line spectrum of the [(MGD)$_2$/Fe—$^{15}$NO] complex (●) is superimposed with the three-line spectrum of the [(MGD)$_2$/Fe—$^{14}$NO] complex (○). The dotted three-line spectrum of the [(MGD)$_2$/Fe—$^{14}$NO] complex was obtained when $^{15}$N-arginine was omitted from the injection solutions. Each spectrum was an average of nine 30-s scans.

FIG. 4B presents spectra obtained from kidney tissue. The spectrum shown was the average of nine 30-s scans.

FIG. 5A and FIG. 5B are graphical presentations of the effect of NMMA on ex vivo 9.5-GHz EPR spectra of [(MGD)$_2$/Fe—NO] complex in the urine of LPS-treated mice. At 6 hours after LPS treatment, the mice were injected with 0.4 mL of [(MGD)$_2$/Fe] complex (326 mg/Kg of MGD and 34 mg/Kg of FeSO$_4$), with or without i.p. injection of NMMA (50 mg/kg). The mice were sacrificed 2 hours after injection of [(MGD)$_2$/Fe] complex. The urine samples were collected and EPR measurements carried out at 22° C.

FIG. 5A presents results where [(MGD)$_2$/Fe] complex alone was injected.

FIG. 5B presents results where [(MGD)$_2$/Fe] complex and NMMA (50 mg/kg) were injected. Note: The NMMA administration inhibited in vivo NO production, thereby markedly reducing the signal intensity of the [(MGD)$_2$/Fe—NO] in the urine.

FIG. 6A presents spectra from the experiment wherein 10 mg of $^{15}$N-arginine were employed. The solid lines in FIG. 3A show a composite of two spectra, i.e., the two-line spectrum of the [(MGD)$_2$/Fe—$^{15}$NO] complex (●) and the three-line spectrum of the [(MGD)$_2$/Fe—$^{14}$NO] complex (○). The dotted three-line spectrum of the [(MGD)$_2$/Fe—$^{14}$NO] complex was obtained when $^{15}$N-arginine was omitted from the injection solutions.

FIG. 6B presents spectra from the experiment wherein 5 mg of $^{15}$N-arginine were employed. Note: The signal intensity of the [(MGD)$_2$/Fe—$^{15}$NO] complex (●) decreased by at least one-half compared to that of the [(MGD)$_2$/Fe—$^{14}$NO] complex

DETAILED DESCRIPTION OF THE INVENTION

Figures 1A, 1B, 1C:
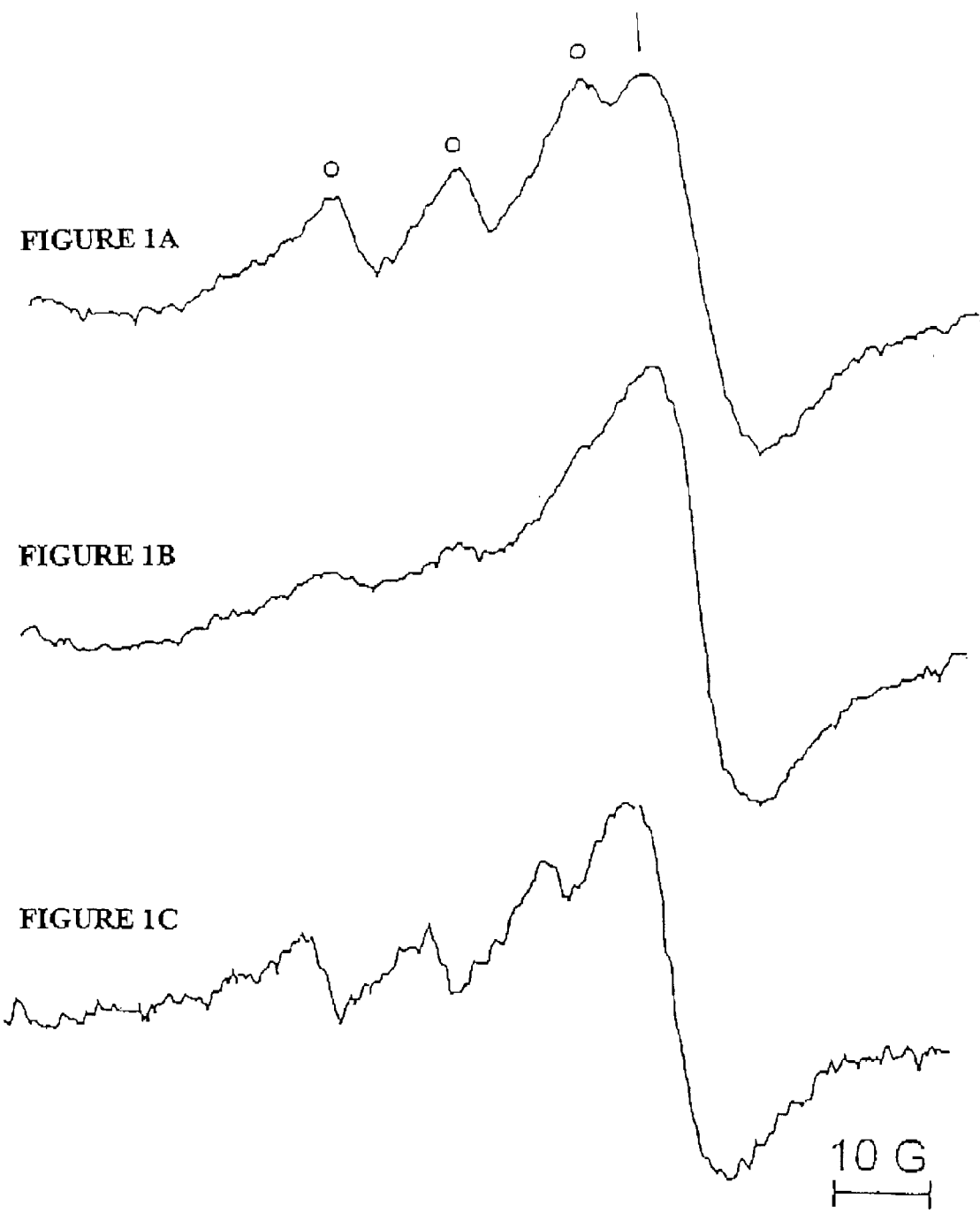
FIG. 1A, FIG. 1B and FIG. 1C illustrate the effects of free radical inhibitors on ex-vivo 9.5-GHz EPR spectra of a [(MGD)$_2$/Fe—NO] complex (MGD is N-methyl-D-glucanine dithiocarbamate) detected in the urine of normal mice. The mice were injected subcutaneously with 0.4 mL of the [(MGD)$_2$/Fe] complex (326 mg/Kg of MGD and 34 mg/Kg of FeSO$_4$) (see FIG. 1A), and in the presence of NMMA (50 mg/kg) (see FIG. 1B), or of dexamethasone (3 mg/kg) (see FIG. 1C). Details of the experimental protocols are described in the Examples. The animals were sacrificed at two hours after injections, and the urine samples collected were transferred to a quartz flat cell for EPR measurement at 22° C. The three-line spectrum of the [(MGD)$_2$/Fe] complex is indicated by open circles (○), and a broad EPR line which is part of the spectrum of the [(MGD)$_2$/Cu] complex is indicated by an arrow.

In accordance with the present invention, there are provided methods for the in vivo reduction of free radical levels in a subject in need thereof. Invention methods comprise:

administering to a subject in need thereof an effective amount of at least one physiologically compatible compound which non-covalently binds free radical (e.g., a free radical scavenger, a spin trapping agent, and the like).

Physiologically compatible compounds contemplated for use in the practice of the present invention include any physiologically compatible derivative of the dithiocarbamate moiety (i.e., $(R)_2N-C(S)-SH$), chelating agents, and the like.

Suitable dithiocarbamate compounds contemplated for use in the practice of the present invention can be described with reference to generic structure I or II as follows:

$$[R_1R_2N-C(S)-S^-]_x M^{+1, +2, +3} \quad (I)$$

wherein: each of $R_1$ and $R_2$ is independently a $C_1$ up to $C_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, substituted acyl, or $R_1$ and $R_2$ can cooperate to form a 5-, 6- or 7-membered ring including N, $R_1$ and $R_2$, x is 1 or 2, and M is a monovalent cation when x is 1, or M is a physiologically compatible divalent or trivalent transition metal cation when x is 2, or

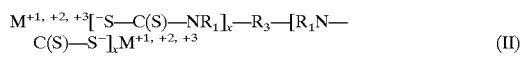

$$M^{+1, +2, +3}[-S-C(S)-NR_1]_x-R_3-[R_1N-C(S)-S^-]_x M^{+1, +2, +3} \quad (II)$$

wherein:

each of $R_1$ is independently selected from a $C_1$ up to $C_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, $R_3$ is a divalent moiety selected from the group consisting of alkylene, substituted alkylene, oxyalkylene, substituted oxyalkylene, alkenylene, substituted alkenylene, arylene, substituted arylene, alkarylene, substituted alkarylene, aralkylene and substituted aralkylene, x is 1 or 2, and M is a monovalent cation when x is 1, or M is a physiologically compatible divalent or trivalent transition metal cation when x is 2 or 3.

Presently preferred dithiocarbamates contemplated for use in the practice of the present invention are substantially hydrophilic, thereby facilitating administration and transport in the bloodstream. This is in contrast to dithiocarbamates employed in the past, which are generally hydrophobic, in order to facilitate transport across cell membranes, etc., an activity which is not required of dithiocarbamates employed for reduction of unacceptably high free radical levels.

Presently preferred dithiocarbamate compounds having generic structure I are those wherein:

each of $R_1$ and $R_2$=a $C_1$ up to $C_{12}$ alkyl, substituted alkyl, alkenyl, substituted alkenyl, alkynyl or substituted alkynyl, wherein the substituents are selected from carboxyl, —C(O)H, oxyacyl, phenol, phenoxy, pyridinyl, pyrrolidinyl, amino, amido, hydroxy, nitro or sulfuryl, and $M=Fe^{+2}$ or $Fe^{+3}$, provided that $R_1$ and $R_2$ are not both $C_2$ alkyl.

Especially preferred dithiocarbamate compounds having generic structure I are those wherein:

$R_1$=a $C_2$ up to $C_8$ alkyl or substituted alkyl, wherein the substituents are selected from carboxyl, acetyl, pyridinyl, pyrrolidinyl, amino, amido, hydroxy or nitro, $R_2$ is selected from a $C_1$ up to $C_6$ alkyl or substituted alkyl, or $R_2$ can cooperate with $R_1$ to form a 5-, 6- or 7-membered ring including N, $R_2$ and $R_1$ and $M=Fe^{+2}$, provided that $R_1$ and $R_2$ are not both $C_2$ alkyl.

The presently most preferred dithiocarbamate compounds having generic structure I are those wherein:

$R_1$=a $C_2$ up to $C_8$ alkyl or substituted alkyl, wherein the substituents are selected from carboxyl, acetyl, amido or hydroxy, $R_2$=a $C_1$ up to $C_4$ alkyl or substituted alkyl, and $M=Fe^{+2}$, provided that $R_1$ and $R_2$ are not both $C_2$ alkyl.

When $R_1$ and $R_2$ cooperate to form a 5-, 6- or 7-membered ring, the combination of $R_1$ and $R_2$ can be a variety of saturated or unsaturated 4, 5 or 6 atom bridging species selected from alkenylene or —O—, —S—, —C(O)- and/or —N(R)-containing alkylene moieties, wherein R is hydrogen or a lower alkyl moiety.

Monovalent cations contemplated for incorporation into the above-described dithiocarbamate compounds include $H^+$, $Na^+$, $NH_4^+$, tetraalkyl ammonium, and the like. Physiologically compatible divalent or trivalent transition metal cations contemplated for incorporation into the above-described dithiocarbamate compounds include charged forms of iron, cobalt, copper, manganese, ruthenium, or the like (e.g., $Fe^{+2}$, $Fe^{+3}$, $Co^{+2}$, $Co^{+3}$, $Cu^{+2}$, $Mn^{+2}$, $Mn^{+3}$ or $Ru^{+3}$). In accordance with the present invention, the ratio of dithiocarbamate-species to counter-ion $M^+$ can vary widely. Thus, dithiocarbamate-containing free radical scavenger can be administered without any added metallic counter-ion (i.e., $M=H^+$, or a transition metal cation to dithiocarbamate-species ratio of zero), with ratios of transition metal cation to dithiocarbamate-species up to about 1:2 (i.e., a 2:1 dithiocarbamate:transition metal cation complex) being suitable.

As employed herein, "substituted alkyl" comprises alkyl groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, sulfonyl, sulfonamide, sulfuryl, and the like.

As employed herein, "cycloalkyl" refers to cyclic ring-containing groups containing in the range of about 3 up to 8 carbon atoms, and "substituted cycloalkyl" refers to cycloalkyl groups further bearing one or more substituents as set forth above.

As employed herein, "cycloalkylene" refers to divalent ring-containing groups containing in the range of about 3 up to 8 carbon atoms, and "substituted cycloalkylene" refers to cycloalkylene groups further bearing one or more substituents as set forth above.

As employed herein, "alkylene" refers to saturated, divalent straight or branched chain hydrocarbyl groups typically having in the range of about 2 up to 12 carbon atoms, and "substituted alkylene" refers to alkylene groups further bearing one or more substituents as set forth above.

As employed herein, "alkenyl" refers to straight or branched chain hydrocarbyl groups having at least one carbon—carbon double bond, and having in the range of about 2 up to 12 carbon atoms, and "substituted alkenyl" refers to alkenyl groups further bearing one or more substituents as set forth above.

As employed herein, "alkenylene" refers to divalent straight or branched chain hydrocarbyl groups having at least one carbon—carbon double bond, and typically having in the range of about 2 up to 12 carbon atoms, and "substituted alkenylene" refers to alkenylene groups further bearing one or more substituents as set forth above.

As employed herein, "alkynyl" refers to straight or branched chain hydrocarbyl groups having at least one carbon—carbon triple bond, and having in the range of about 2 up to 12 carbon atoms, and "substituted alkynyl" refers to alkynyl groups further bearing one or more substituents as set forth above.

As employed herein, "aryl" refers to aromatic groups having in the range of 6 up to 14 carbon atoms and "substituted aryl" refers to aryl groups further bearing one or more substituents as set forth above.

As employed herein, "alkylaryl" refers to alkyl-substituted aryl groups and "substituted alkylaryl" refers to alkylaryl groups further bearing one or more substituents as set forth above.

As employed herein, "arylalkyl" refers to aryl-substituted alkyl groups and "substituted arylalkyl" refers to arylalkyl groups further bearing one or more substituents as set forth above.

As employed herein, "arylalkenyl" refers to aryl-substituted alkenyl groups and "substituted arylalkenyl" refers to arylalkenyl groups further bearing one or more substituents as set forth above.

As employed herein, "arylalkynyl" refers to aryl-substituted alkynyl groups and "substituted arylalkynyl" refers to arylalkynyl groups further bearing one or more substituents as set forth above.

As employed herein, "arylene" refers to divalent aromatic groups typically having in the range of 6 up to 14 carbon atoms and "substituted arylene" refers to arylene groups further bearing one or more substituents as set forth above.

As employed herein, "alkarylene" refers to alkyl-substituted divalent aryl groups typically having in the range of about 7 up to 16 carbon atoms and "substituted alkarylene" refers to alkarylene groups further bearing one or more substituents as set forth above.

As employed herein, "aralkylene" refers to aryl-substituted divalent alkyl groups typically having in the range of about 7 up to 16 carbon atoms and "substituted aralkylene" refers to aralkylene groups further bearing one or more substituents as set forth above.

As employed herein, "aralkenylene" refers to aryl-substituted divalent alkenyl groups typically having in the range of about 8 up to 16 carbon atoms and "substituted aralkenylene" refers to aralkenylene groups further bearing one or more substituents as set forth above.

As employed herein, "aralkynylene" refers to aryl-substituted divalent alkynyl groups typically having in the range of about 8 up to 16 carbon atoms and "substituted aralkynylene" refers to aralkynylene groups further bearing one or more substituents as set forth above.

As employed herein, "aroyl" refers to aryl-carbonyl species such as benzoyl and "substituted aroyl" refers to aroyl groups further bearing one or more substituents as set forth above.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As employed herein, "heterocycloalkylene" refers to divalent cyclic (i.e., ring-containing) groups containing one or more heteroatoms (e.g., N, O, S, or the like) as part of the ring structure, and having in the range of 3 up to 14 carbon atoms and "substituted heterocycloalkylene" refers to heterocycloalkylene groups further bearing one or more substituents as set forth above.

As employed herein, "acyl" refers to alkyl-carbonyl species.

As employed herein, "halogen" refers to fluoride, chloride, bromide or iodide atoms.

The dithiocarbamate-containing free radical scavengers employed in the invention method can interact with a variety of free radical species produced under physiological conditions. Such species include nitric oxide, peroxynitrite, superoxide radical, singlet oxygen, hydroxy radical, peroxy radical, and the like. Each of these free radicals can be over- or inappropriately produced in a subject and thereby cause damage to the health of said subject. Nitric oxide (NO) is an exemplary free radical discussed throughout the present specification. However, it should be understood that any discussion or data pertaining to NO is equally applicable to other free radical species.

In accordance with another embodiment of the present invention, there are provided methods for treating free radical overproduction in a subject in need thereof. Invention methods comprise administering to a subject in need thereof an effective amount of at least one physiologically compatible compound which non-covalently binds free radical (e.g., a free radical scavenger, a spin trapping agent, or the like).

Free radical overproduction is associated with a wide range of disease states and/or indications, such as, for example, aging, septic shock, ischemia, administration of cytokines, overexpression of cytokines, ulcers, inflammatory bowel disease (e.g., gastritis, ulcerative colitis or Crohn's disease), diabetes, arthritis (e.g., rheumatoid arthritis), asthma, Alzheimer's disease, Parkinson's disease, multiple sclerosis, cirrhosis, allograft rejection (e.g., transplant rejection), encephalomyelitis, meningitis, pancreatitis, peritonitis, vasculitis, lymphocytic choriomeningitis, glomerulonephritis, ophthalmologic diseases (e.g., uveitis, glaucoma, blepharitis, chalazion, allergic eye disease, corneal ulcer, keratitis, cataract, retinal disorders, age-related macular degeneration, optic neuritis, and the like), ileitis, inflammation induced by overproduction of inflammatory cytokines (e.g., liver inflammation, renal inflammation, airway inflammation, and the like), hemorrhagic shock, anaphylactic shock, burn, infection leading to the overproduction of inflammatory cytokines (including bacterial (e.g., *E. coli* infection), viral (e.g., HIV), fungal (e.g., Candidiosis and histoplasmosis) and parasitic (e.g., Leishmaniasis and Schistosomiasis) infections), hemodialysis, chronic fatigue syndrome, stroke, cancers (e.g., breast, melanoma, carcinoma, and the like), cardiovascular diseases associated with overproduction of inflammatory cytokines (e.g., heart disease, cardiopulmonary bypass, ischemic/reperfusion injury, and the like), ischemic/reperfusion associated with overproduction of inflammatory cytokines, toxic shock syndrome, adult respiratory distress syndrome, cachexia, myocarditis, autoimmune disorders, eczema, psoriasis, heart failure, dermatitis, urticaria, cerebral ischemia, systemic lupus erythematosis, AIDS, AIDS dementia, neurodegenerative disorders (e.g., chronic neurodegenerative disease), chronic pain, priapism, cystic fibrosis, amyotrophic lateral sclerosis, schizophrenia, depression, premenstrual syndrome, anxiety, addiction, migraine, Huntington's disease, epilepsy, gastrointestinal motility disorders, obesity, hyperphagia, solid tumors (e.g., neuroblastoma), malaria, hematologic cancers, myelofibrosis, lung injury, graft-versus-host disease, head injury, CNS trauma, hepatitis, renal failure, liver disease (e.g., chronic hepatitis C), drug-induced lung injury (e.g., paraquat), transplant rejection and preservation, fertility enhancement, bacterial translocation, circulatory shock, traumatic shock, vascular aneurysm (e.g., aortic aneurysm), lack of immune response to vaccination, ileus, myocardial infarction, cerebral vasospasms, hearing loss, organ preservation, and the like.

With particular reference to cytokine therapy, the invention method will find widespread use because cytokine therapy (with consequent induction of free radical overproduction) is commonly used in the treatment of cancer and AIDS patients. Systemic hypotension due to the induction of free radical overproduction is a dose-limiting side effect of cytokine therapy. Thus, a large patient population exists which will benefit from the invention methods.

Presently preferred indications for treatment in accordance with the present invention include septic shock, ischemia, administration of IL-1, administration of IL-2, administration of IL-6, administration of IL-12, administration of tumor necrosis factor, administration of interferon-gamma, ulcers, ulcerative colitis, diabetes, arthritis, asthma, Alzheimer's disease, Parkinson's disease, multiple sclerosis, cirrhosis or allograft rejection. Especially preferred indications for treatment in accordance with the present invention include free radical overproduction associated with septic shock and free radical overproduction associated with cytokine therapy.

In accordance with a particular aspect of the present invention, the free radical scavenger is administered in combination with a cytokine (e.g., an interleukin (e.g., IL-1, IL-2, IL-6 or IL-12), TNF or an interferon (e.g., interferon-, interferon-, and the like)), an antibiotic (e.g., gentamicin, tobramycin, amikacin, piperacillin, clindamycin, cefoxitin or vancomycin, or mixtures thereof), a vasoactive agent (e.g., a catecholamine, noradrenaline, dopamine or dobutamine), or mixtures thereof. In this way, the detrimental side effects of many of the above-noted pharmaceutical agents (e.g., systemic hypotension) can be prevented or reduced by the use of the above-described free radical scavenger. Thus, a patient being treated with any of the above-described agents could be monitored for evidence of free radical overproduction (e.g., blood pressure drop). At the first evidence of such overproduction, co-administration of a suitable dose of the above-described free radical scavenger could be initiated, thereby alleviating (or dramatically reducing) the side-effects of the primary therapy.

Those of skill in the art recognize that the free radical scavengers described herein can be delivered in a variety of ways, such as, for example, orally, transdermally, intravenously, intramuscularly, subcutaneously, parenterally, rectally, by inhalation, and the like.

Since individual subjects may present a wide variation in severity of symptoms and each drug has its unique therapeutic characteristics, the precise mode of administration and dosage employed for each subject is left to the discretion of the practitioner. In general, the dosage of free radical scavenger employed in the practice of the present invention falls in the range of about 0.01 mmoles/kg body weight of the subject/hour up to about 0.5 mmoles/kg/hr.

Depending on the mode of delivery employed, the free radical scavengers contemplated for use herein can be delivered in a variety of pharmaceutically acceptable forms. For example, the scavenger can be delivered in the form of a solid, solution, emulsion, dispersion, micelle, liposome, and the like.

Pharmaceutical compositions of the present invention can be used in the form of a solid, a solution, an emulsion, a dispersion, a micelle, a liposome, and the like, wherein the resulting composition contains one or more of the compounds of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. The active compound(s) (e.g., one or more compounds of structure I and/or structure II as described herein) is(are) included in the pharmaceutical composition in an amount sufficient to produce the desired effect upon the process or disease condition.

Pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing the active ingredient in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Compounds contemplated for use in the practice of the present invention may also be administered in the form of suppositories for rectal administration of the drug. These compositions may be prepared by mixing the drug with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, it is up to the practitioner to determine a subject's response to treatment and vary the dosages accordingly.

Typical daily doses, in general, lie within the range of from about 10 g up to about 100 mg per kg body weight, and, preferably within the range of from 50 g to 10 mg per kg body weight and can be administered up to four times daily. The daily IV dose lies within the range of from about 1 g to about 100 mg per kg body weight, and, preferably, within the range of from 10 g to 10 mg per kg body weight.

As readily recognized by those of skill in the art, a given compound can exist as a mixture of different ionized forms thereof, such that some proportion of the bis (dithiocarbamate) can be present, for example, as a sodium salt, while some proportion of the bis(dithiocarbamate) can be present as an iron chelate. It is presently preferred that the ratio of iron to bis(dithiocarbamate) fall in the range of about zero up to about 1:1.

The invention will now be described in greater detail by reference to the following non-limiting examples.

EXAMPLE 1

ICR Mice (female, 20–30 g) Were Supplied by Harlan Sprague-Dawley (Indianapolis, Ind.).

Dexamethasone, lipopolysaccharide (LPS; *E. coli* 026:B6) and acetylcholine chloride were obtained from Sigma (St. Louis, Mo.). $^{15}N_2$-guanido-L-arginine ($^{15}N$-arginine) was purchased from Cambridge Isotope Laboratories (Woburn, Mass.). $N^G$-monomethyl-L-arginine (NMMA) was obtained from Calbiochem (San Diego, Calif.). Methoxyflurane was obtained from Pitman-Moore (Mundelein, Ill.).

Pure NO gas was purchased from Matheson (Joliet, Ill.) and pure argon gas was obtained from Airco (Murray Hill, N.J.). Saturated NO solution in water was prepared by following the method of Kelm and Schrader, supra.

The concentration of the saturated NO solution is 2.0 mM, as verified by an ISO-NO meter from World Precision Instruments (Sarasota, Fla.). $NO_2^-$ was measured by a calorimetric assay (Green et al., *Anal. Biochem.* 126:131–138 (1982)). $NO_3^-$ was first converted to $NO_2^-$ by *E. coli* nitrate reductase (Bartholomew, B., *Fd. Chem. Toxic.* 22:541–543 (1984)) and measured as described above.

N-Methyl-D-glucamine and carbon disulfide were obtained from Aldrich (Milwaukee, Wis.). N-Methyl-D-glucamine dithiocarbamate (MGD) was synthesized by following the method of Shinobu et al. (*Acta Pharmacol. Toxicol.* 54:189–194 (1984)).

EXAMPLE 2

EPR Measurement of Nitric Oxide Levels

A. In Vivo Measurement of [(MGD)$_2$/FE-NO] Levels in the Circulation of the LPS-treated Mice.

Noninvasive in vivo EPR spectra were recorded with an EPR spectrometer equipped with an S-band microwave bridge and a low-frequency loop-gap resonator with a 4-mm loop with a length of 1 cm, operating at 3.5 GHz (Froncisz and Hyde, *J. Magn. Reson.* 47:515–521 (1982)). Instrument settings include 100-G field scan, 30-s scan time, 0.1-s time constant, 2.5-G modulation amplitude, 100-KHz modulation frequency and 25-mW microwave power. The measured unloaded Q of the empty resonator was 3000 and the loaded Q was 400 (with the presence of the mouse tail). Other instrument settings and experimental conditions have been described previously (Komarov et al., Biochem. Biophys. Res. Comm. 195:1191–1198, 1993 and Lai and Komarov, FEBS Lett. 345:120–124, 1994).

For measurement of $^{15}NO$ production, at 6 h after i.v. injection of LPS (6 mg/mouse) via the lateral tail vein, the mice were anesthetized with methoxyflurane prior to subcutaneous injections of $^{15}N$-arginine (5 or 10 mg per mouse) in saline, and of 0.4 ml of the [(MGD)$_2$/Fe] complex (326 mg/kg of MGD and 34 mg/kg of FeSO$_4$) in water. Injections of [(MGD)$_2$/Fe] complex at levels up to 1% body weight did not affect the survival of the mice (Lai and Komarov, supra). Immediately after injection, the mouse housed in a plexiglass restraining tube was transferred to the S-band EPR spectrometer and the tail of the mouse was immobilized by taping down with a thin and narrow plexiglass stick and then placed inside the resonator; no anesthetic agent was used. The in vivo EPR signal was recorded at 2 h after the injection of the [(MGD)$_2$/Fe] complex (Lai and Komarov, supra).

For inhibition experiments, at 6 h after LPS treatment, mice were injected intraperitoneally with an aliquot of 50 mg/kg N-monomethyl-L-arginine (NMMA) in saline. NMMA is an inhibitor of both constitutive and inducible synthase activities (Aisaka et al., Biochem. Biophys. Res. Comm. 60:881–886, 1989 and Rees et al., Proc. Natl. Acad. Sci. USA 86:3375–3379, 1989). In other experiments, at 1.5 h prior to LPS challenge, mice were injected intravenously with 3 mg/kg dexamethasone in saline. Dexamethasone is an inhibitor of inducible NO synthase, but not constitutive NO synthase (Rees et al., *Biochem. Biophys. Res. Commun.* 173:541–547 (1990)). The in vivo EPR signal was also recorded at 2 h after the injection of [(MGD)$_2$/Fe] complex (Lai and Komarov, supra).

B. Ex vivo Measurements of [(MGD)$_2$/Fe—NO] Levels in the Urine of Normal Mice.

Normal mice housed in a restraining tube were injected subcutaneously with 0.4 ml of the [(MGD)$_2$/Fe] complex (326 mg/Kg of MGD and 34 mg/Kg of FeSO$_4$). After 2 hours, the animals were sacrificed and the urine samples were collected from the urinary bladder. The urine sample, which was dark brown (characteristic of the presence of [(MGD)$_2$/Fe] complex), was transferred to a quartz flat cell for EPR measurement. The spectra were recorded at 22° C. with an X-band EPR spectrometer, operating at 9.5 GHz. Instrument settings include 100-G field scan, 4-min scan time, 0.5-s time constant, 2.5-G modulation amplitude, 100-KHz modulation frequency and 100-mW microwave power. The concentrations of the [(MGD)$_2$/Fe—NO] complex in the urine samples were calculated by comparing the signal intensities obtained from the samples to the signal intensity of a standard solution containing 0.1 mM of the [(MGD)$_2$/Fe—NO] complex.

For inhibition experiments, mice were injected intraperitoneally with 50 mg/kg NMMA in saline immediately after the injection of the [(MGD)$_2$/Fe] complex. In other experiments, mice were injected intravenously with 3 mg/kg dexamethasone in saline about 1.5 h before the injection of the [(MGD)$_2$/Fe] complex. For measurement of $^{15}$NO production in normal mice, mice were injected subcutaneously with $^{15}$N-arginine (5 or 10 mg/mouse) in saline immediately before the injection of the [(MGD)$_2$/Fe] complex. Acetylcholine chloride (Sigma) in saline was freshly prepared prior to subcutaneous injection at a dose of 67 mg/kg.

C. Ex vivo Measurement of [(MGD)$_2$/Fe—NO] Levels in the Urine of LPS-treated Mice.

At 0, 2, 4, 6 or 8 h after LPS treatment (6 mg/mouse; at least three animals in each group), the mice housed in a restraining tube were anesthetized with methoxyflurane prior to subcutaneous injection with 0.4 ml of the [(MGD)$_2$/Fe] complex (326 mg/Kg of MGD and 34 mg/Kg of FeSO$_4$). After 2 h, the mouse was sacrificed and the urine sample was collected from the urinary bladder, and immediately transferred to a quartz flat cell for X-band EPR measurement as described above in Example 2B. Inhibition experiments with NMMA or dexamethasone were performed as described above in Example 2A, except that the mice were treated with LPS prior to following the protocols for NO inhibition experiments. The procedures for S-band EPR measurement of wet tissues and blood samples were as described previously (Lai and Komarov, supra).

EXAMPLE 3

Detection of the [(MGD)l/Fe—NO] Complex in the Urine of Normal Mice

At 2 h after subcutaneous injection of an aliquot (0.4 ml) of the [(MGD)$_2$/Fe] complex (326 mg/Kg of MGD and 34 mg/Kg of FeSO$_4$) into normal mice (A) (and also in the presence of NMMA (50 mg/kg) (B), or of dexamethasone (3 mg/kg) (C)), the animals were sacrificed and the urine samples collected and transferred to a quartz flat cell for X-band (9.5 GHz) EPR measurement at 22° C. The spectrum of the urine samples was found to be composed of two components, a three-line spectrum ($\alpha^N$=12.5 G and $g_{ISO}$= 2.04) characteristic of the [(MGD)$_2$/Fe—NO] complex, and a strong broad signal (See FIG. 1A). The strong broad signal is part of the EPR spectrum of the [(MGD)$_2$/Cu] complex present in the urine, resulting from the chelation of urinary copper by the excreted MGD molecule. The concentration of the [(MGD)$_2$/Fe—NO] complex detected in the urine sample of normal mice is estimated to be 1.3 M (see Table 1).

TABLE 1

Quantitation of the amounts of [(MGD)$_2$/Fe-NO] present in mouse urine under various conditions

| Conditions | [(MGD $_2$/Fe-NO], $\mu$M$^a$ |
|---|---|
| Controls | 1.3 ± 0.2 (8)$^b$ |
| + NMMA (50) mg/kg | 0.4 ± 0.3 (8)* |

TABLE 1-continued

Quantitation of the amounts of [(MGD)$_2$/Fe-NO] present in mouse urine under various conditions

| Conditions | [(MGD $_2$/Fe-NO], $\mu$M$^a$ |
|---|---|
| + Acetylcholine (67) mg/kg) | 3.9 ± 0.8 (3)* |
| + Dexamethasone | 1.4 ± 0.3 (7) |

The amounts of the [(MGD) $_2$/Fe-NO] complex in mouse urine were calculated by comparing the EPR signal intensities of mouse urine with the signal intensity of a standard solution containing known concentration of [(MGD) $_2$/Fe-NO].
The data presented are mean ± S.E. (number of mice).
* P < 0.05 compared with controls.

Simultaneous injection of [(MGD)$_2$/Fe] and NMMA markedly reduced the [(MGD)$_2$/Fe—NO] signal in the urine samples, see FIG. 1B and Table 1. On the other hand, as noted in FIG. 1C and Table 1, injection of [(MGD)$_2$/Fe] into mice pretreated with dexamethasone produced negligible effects on the [(MGD)$_2$/Fe—NO] signal.

These results suggest that the NO detected in normal mouse urine in the form of the [(MGD)$_2$/Fe—NO] complex was produced by constitutive NO synthase, but not by inducible NO synthase.

To further verify this suggestion, the effect of acetylcholine, a vasodilatory agent which is known to effect the basal NO level, but not the inducible NO level (Aisaka et al., *Biochem. Biophys. Res. Commun.* 163:710–717 (1989); Whittle et al., *Br. J. Pharmacol.* 98:646–652 (1989); and Vicaut et al., *J. Appl. Physiol.* 77:536–533 (1994)), was tested on the urinary [(MGD)$_2$/Fe—NO] level of normal mice. Injection of acetylcholine was found to produce a 3-fold increase in urinary [(MGD)$_2$/Fe—NO] levels (see Table 1). This observation represents the first direct in vivo evidence to confirm that the endothelium-derived relaxation factor released by acetylcholine (the Furchgott phenomenon) is indeed nitric oxide.

The question is raised whether the NO detected in normal mouse urine (Example 3) and the NO trapped by the [(MGD)$_2$/Fe] complex (Table 1) is a result of the injection of the [(MGD)$_2$/Fe] complex. In other words, does the injection of the complex alone enhance the NO production in vivo? In the previous experiments, it has been shown that the intravenous injection of the [(MGD)$_2$/Fe] complex did not affect the mean arterial pressure of mice (Komarov, et al. supra), suggesting that the complex by itself does not seem to affect the in vivo NO production.

EXAMPLE 4

It is well established in the art that L-arginine is converted into NO and citrulline by NO synthase enzymes (Ignarro, L. J., supra; Moncada, S., supra; and Lowenstein and Snyder, supra). To determine the origin of NO detected in normal mouse urine, $^{15}$N-arginine (10 mg/mouse) and [(MGD)$_2$/Fe] were injected simultaneously, and the EPR signal in the resulting urine sample was measured, as described above. Thus, mice were injected with 0.4 ml of the [(MGD)$_2$/Fe] complex (326 mg/Kg of MGD and 34 mg/Kg of FeSO$_4$) with (A) 10 mg 5N-arginine or (B) 5 mg $^{15}$N-arginine. The animals were sacrificed at 2 h after injection, and the urine samples were transferred to a quartz flat cell for EPR measurement at 22° C.

It was reasoned that if the NO detected in normal mouse urine comes from the arginine-NO synthase pathway, upon injection of $^{15}$N-arginine, one should expect to detect the $^{15}$NO in the form of the [(MGD)$_2$/Fe—$^{15}$NO] complex in the urine. This indeed was the case as seen by EPR, in which the two-line spectrum of the [(MGD)$_2$/Fe—$^{15}$NO] complex was detected in the urine, along with a weak three-line spectrum of the [(MGD)$_2$/Fe—$^{14}$NO] complex (FIG. 2A, the solid lines); the $^{14}$NO was generated by the same enzymatic pathway, except utilizing endogenous $^4$N-arginine as a substrate. This suggests that subcutaneously injected $^{15}$N-arginine competes effectively with endogenous $^{14}$N-arginine as a substrate for NO synthases. When $^{15}$N-arginine was omitted from the injection solution, the typical three-line spectrum of the [(MGD)$_2$/Fe—$^{14}$NO] complex became more visible (see FIG. 2A, dotted lines).

Figures 2A, 2B:
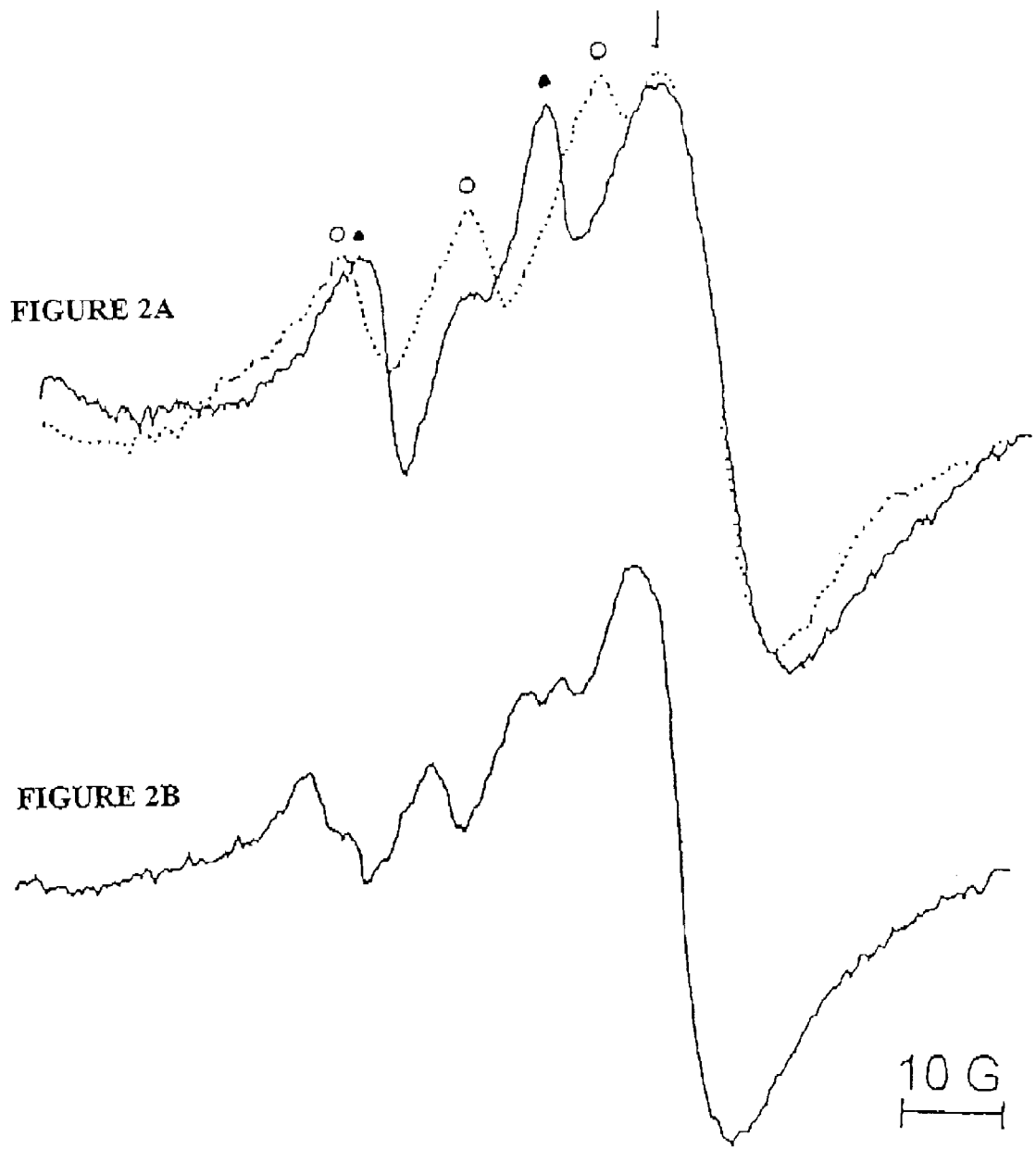
FIG. 2A and FIG. 2B present ex-vivo 9.5 GHz EPR spectra of [(MGD)$_2$/Fe—$^{15}$NO] and [(MGD)$_2$/Fe—$^{14}$NO] complexes present in the urine of normal mice injected with $^{15}$N-arginine. The mice were injected with 0.4 mL of the [(MGD)$_2$/Fe] complex (326 mg/Kg and 34 mg/Kg of FeSO$_4$) with (see FIG. 2A) 10 mg $^{15}$N-arginine or (see FIG. 2B) 5 mg $^{15}$N-arginine. The animals were sacrificed at two hours after injections, and the urine samples were transferred to a quartz flat cell for EPR measurement at 22° C. Note: The two-line spectrum of the [(MGD)/Fe—$^{15}$NO] complex is indicated by closed circles (●). The dotted lines of the [(MGD)$_2$/Fe—$^{14}$NO] spectrum in A as indicated by open circles (○) were obtained without the injection of $^{15}$N-arginine. The receiver gain for A was 1.3 times higher than that of B and the rest of the experimental conditions were the same as described with respect to FIG. 1A, FIG. 1B and FIG. 1C.

On the other hand, when the amount of $^{15}$N-arginine injected (5 mg/mouse) was reduced by one-half, the signal intensity of the [(MGD)$_2$/Fe—$^{15}$NO] complex decreased compared to that of the [(MGD)$_2$/Fe—$^{14}$NO] complex (see FIG. 2B). Therefore, it can be concluded that the [(MGD)$_2$/Fe] complex injected subcutaneously into normal mice interacts with the NO produced in tissues through the arginine-constitutive NO synthase pathway to form the [(MGD)$_2$/Fe—NO] complex, which is eventually concentrated in the urine and excreted.

EXAMPLE 5

Detection of the [(MGD)$_2$/Fe—NO] Complex in the Blood Circulation of LPS-treated Mice It has previously been shown that upon bolus infusion of LPS (6 mg/mouse), mice are in septic-shock like conditions within 6 h, as indicated by a gradual fall in mean arterial pressure from 121 3 mm Hg to 85 7 mm Hg (Lai and Komarov, supra). In addition, it has been shown that at 6 h after LPS treatment, the in vivo three-line spectrum of the [(MGD)$_2$/Fe—NO] complex (wherein [(MGD)$_2$/Fe] is injected subcutaneously 2 h before EPR measurement) is observed in the circulation of the mouse tail, as detected by S-band EPR spectroscopy (Lai and Komarov, supra).

To further ascertain the chemical nature of NO detected in LPS-treated mice, $^{15}$N-arginine (10 mg/kg) was injected, together with 0.4 ml of the [(MGD)$_2$/Fe] spin-trapping reagent (326 mg/Kg of MGD and 34 mg/Kg of FeSO$_4$), into LPS-treated mice and measured in vivo by S-band EPR spectrum. The in vivo S-band EPR spectra were recorded 2 h after administration of the [(MGD)$_2$/Fe] complex.

Figure 3A:
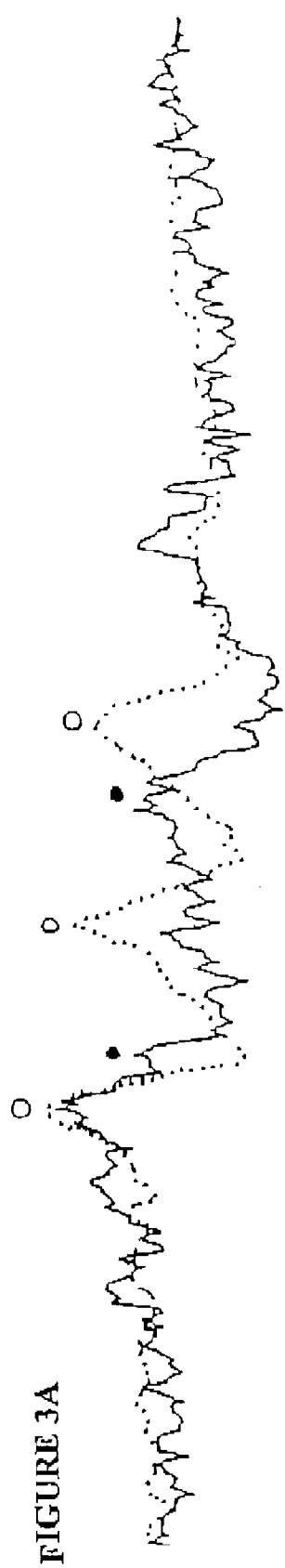
FIG. 3A and FIG. 3B present in vivo 3.5-GHz EPR spectra of [(MGD)$_2$/Fe—NO] complex in the circulation. At 6 hours after LPS administration, the mice were injected with 10 mg of $^{15}$N-arginine in saline and 0.4 mL of the [(MGD)$_2$/Fe] complex. The in vivo S-band EPR spectra were recorded 2 hours after the [(MGD)$_2$/Fe] administration (the solid lines).
Figure 3B:
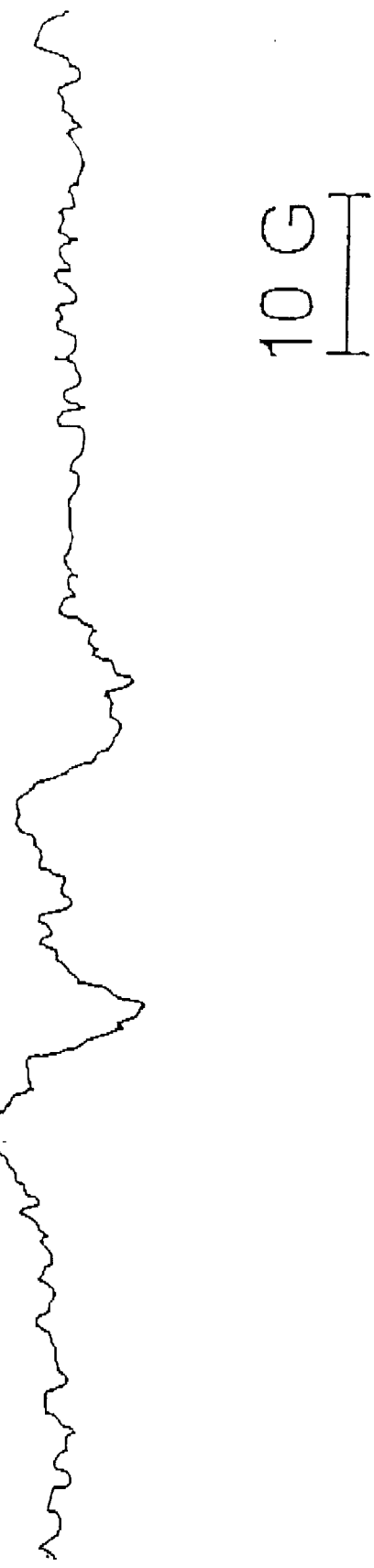

Albeit weak, the in vivo two-line spectrum of the [(MGD)$_2$/Fe$^{15}$-NO] complex in the circulation of the mouse tail was clearly visible (FIG. 3A, the solid lines), further confirming that the detected NO in the form of the [(MGD)$_2$/Fe—NO] complex in LPS-treated mice was produced via the arginine-NO synthase pathway. The three-line spectrum typical of the [(MGD)$_2$/Fe—$^{14}$NO] complex was obtained when $^{15}$N-arginine was omitted (FIG. 3A, the dotted lines). The mice treated with $^{15}$N-arginine were sacrificed, and the whole blood obtained was transferred for X-band EPR measurement at 22° C. The EPR signal of the whole blood obtained from $^{15}$N-arginine treated mice (FIG. 3B) is identical to that of the solid lines of FIG. 3A. This suggests that the EPR signal in FIG. 3A or FIG. 3B is attributed to the [(MGD)$_2$/Fe—NO] complex circulating in the blood, rather than trapped in the tail muscle at or near the site of the injection.

Figures 4A, 4B:
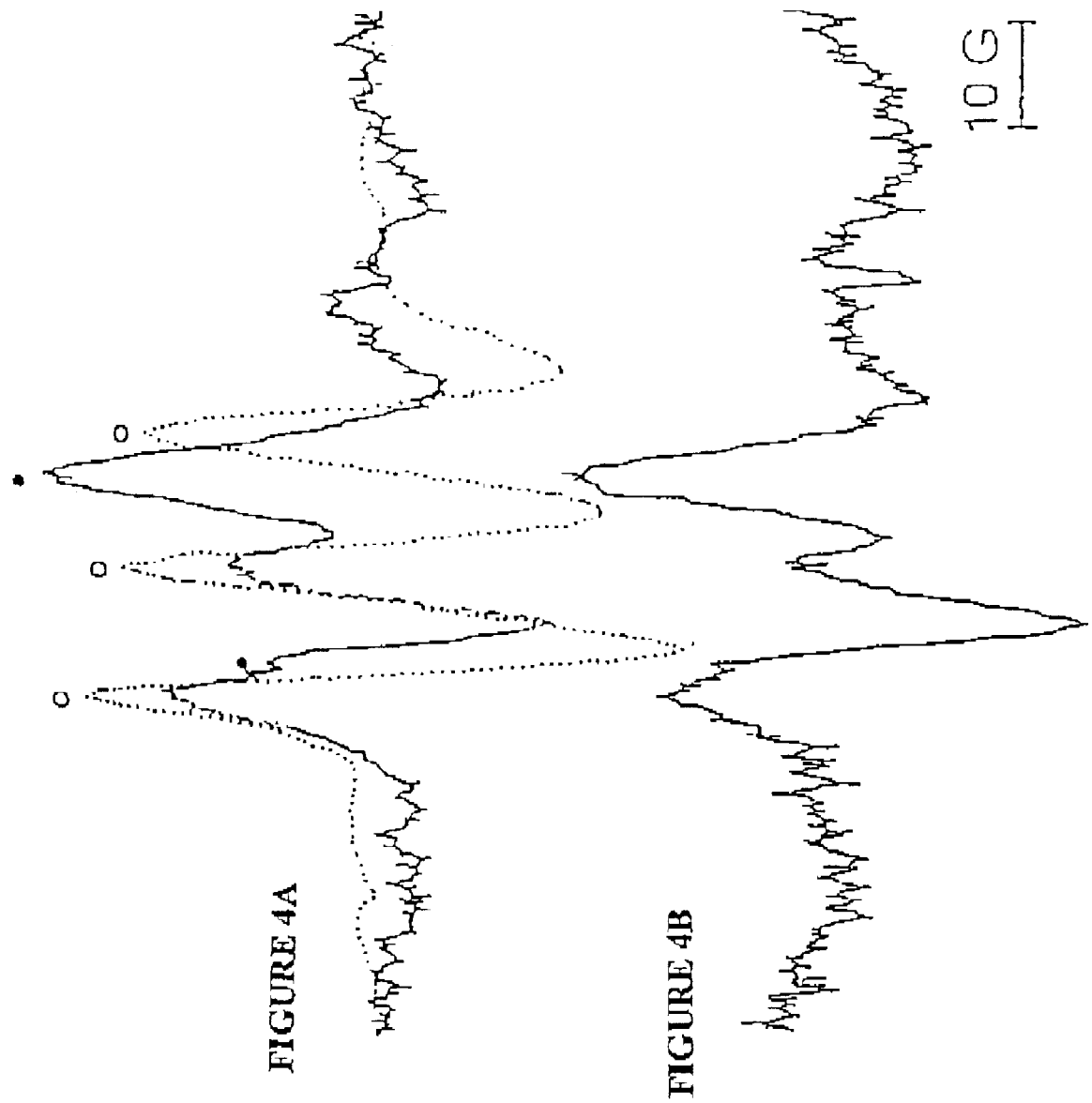
FIG. 4A and FIG. 4B present ex vivo 3.5-GHz EPR spectra of [(MGD)$_2$/Fe—$^{15}$NO] and [(MGD)$_2$/Fe—$^{14}$NO] complexes detected in various tissues of LPS-treated mice after intravenous injection of $^{15}$N-arginine. Six hours after LPS administration, the mice were injected with 10 mg of $^{15}$N-arginine in saline and 0.4 ml of the [(MGD)$_2$/Fe] complex (326 mg/Kg of MGD and 34 mg/Kg of FeSO$_4$). Two hours after administration of the [(MGD)$_2$/Fe] complex, the mice were sacrificed and wet tissues transferred to quartz tubes (i.d. 2 mm) for EPR measurement at 22° C.

The S-band EPR signal of the [(MGD)$_2$/Fe—$^{15}$NO] complex was also detected in various isolated tissues obtained from LPS-treated mice injected with the [(MGD)$_2$/Fe] complex and $^{15}$N-arginine (FIG. 4A and FIG. 4B). Thus, the two-line spectrum characteristic of [(MGD)$_2$/Fe—$^{15}$NO], superimposed with the three-line spectrum characteristic of [(MGD)$_2$/Fe—$^{14}$NO], were observed in the liver and kidneys (see FIGS. 4A and 4B, respectively). Again, the spectrum characteristic of the [(MGD)$_2$/Fe—$^{14}$NO] complex was detected in the mouse liver when $^{15}$N-arginine was omitted from the injection fluid (see FIG. 4A, the dotted lines).

EXAMPLE 6

Detection of the [(MGD)$_2$/Fe—NO] Complex in the Urine of LPS-treated Mice

The effects of NMMA on ex vivo 9.5-GHz EPR spectra of the [(MGD)$_2$/Fe—NO] complex in the urine of the LPS-treated mice were determined. Thus, at 6 h after LPS treatment, mice were injected with the [(MGD)$_2$/Fe] complex, with and without i.p. injection of NMMA (50 mg/kg). The mice were sacrificed at 2 h after injection of the [(MGD)$_2$/Fe] complex. The urine samples were collected and the EPR measurement was carried out at 22° C.

A strong three-line spectrum characteristic of the [(MGD)$_2$/Fe—NO] complex was detected in the urine sample obtained from the LPS-treated mouse injected with the [(MGD)$_2$/Fe] complex (see FIG. 5A). The concentration of the complex is estimated to be 35.1 M at 8 h after LPS challenge; the [(MGD)$_2$/Fe] complex was injected at 6 h after LPS.

Injection of NMMA markedly reduces the signal intensity (FIG. 5B) as well as the amounts of the [(MGD)$_2$/Fe—NO] complex (Table 2), which is consistent with the notion that the NO trapped by the [(MGD)$_2$/Fe] complex injected in the LPS-treated mice is produced mainly by inducible NO synthase. Thus, inducible NO synthase activities in living animals may be reduced by treatment with NO trapping agents as described herein.

Figure 6A:
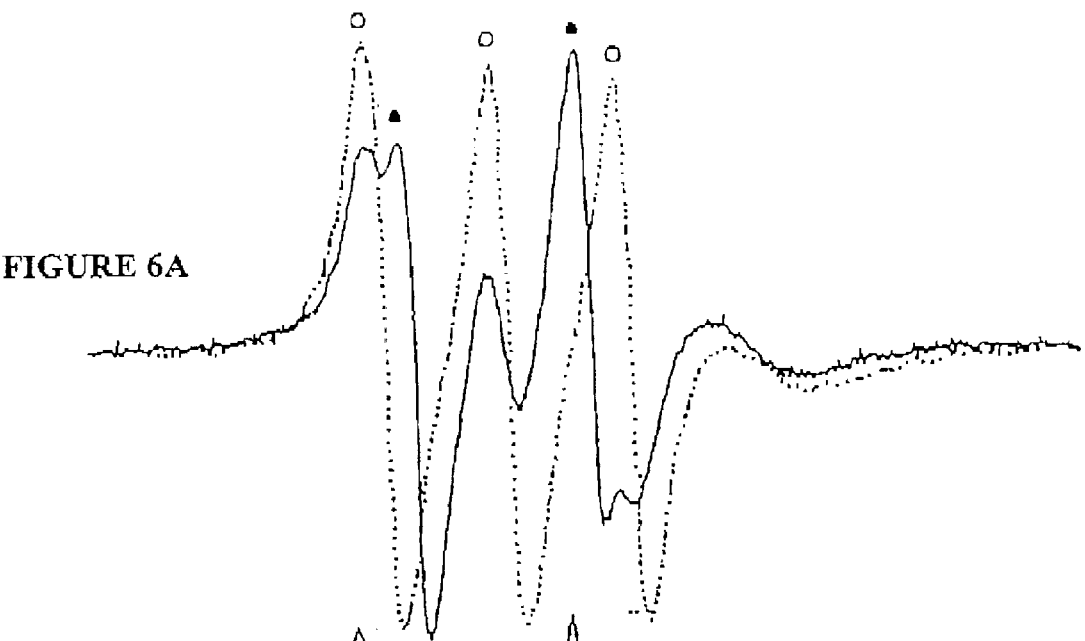
FIG. 6A and FIG. 6B present ex vivo 9.5-GHz EPR spectra of [(MGD)$_2$/Fe—$^{15}$NO] and [(MGD)$_2$/Fe—$^{14}$NO] complexes in the urine of LPS-treated mice injected with $^{15}$N-arginine. Six hours after LPS administration, the mice were injected with 5 or 10 mg of $^{15}$N-arginine in saline and 0.4 ml of the [(MGD)$_2$/Fe] complex (326 mg/Kg of MGD and 34 mg/Kg of FeSO$_4$). Urine samples were collected two hours after administration of the [(MGD)$_2$/Fe] complex, and transferred to quartz tubes (i.d. 2 mm) for EPR measurement at 22° C.
Figure 6B:
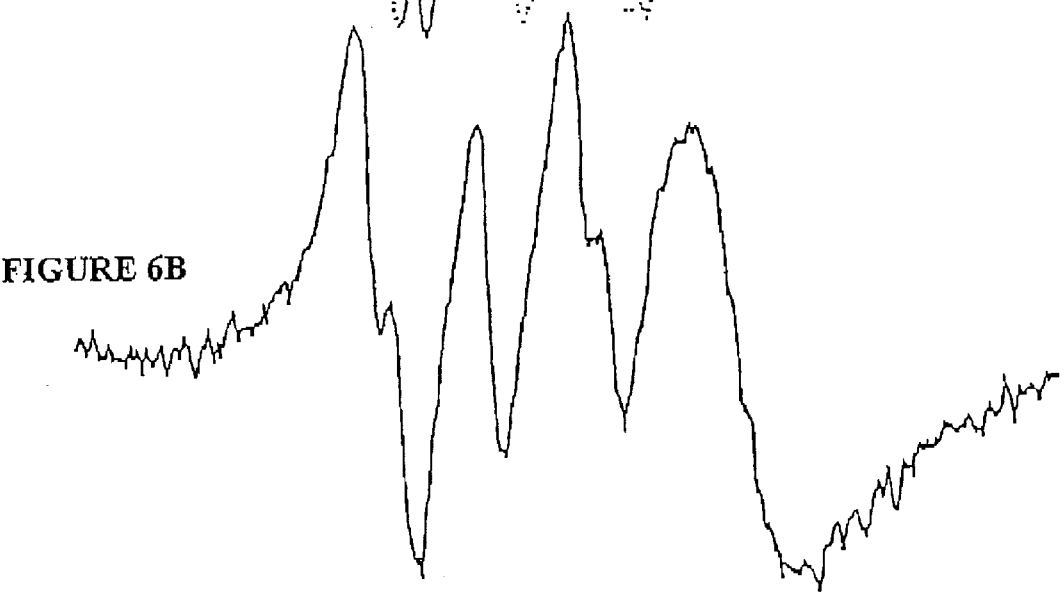

Furthermore, simultaneous injection of $^{15}$N-arginine (10 mg/mouse) and the [(MGD)$_2$/Fe] complex into the LPS-treated mice gave rise to a composite EPR spectrum, consisting of a two-line spectrum of the [(MGD)$_2$/Fe—$^{15}$NO] complex (closed circles), and a three-line spectrum of the [(MGD)$_2$/Fe—$^{14}$NO] complex (open circles) as shown in FIG. 6A (the solid lines). The pure three-line spectrum of the [(MGD)$_2$/Fe—$^{14}$NO] complex as depicted by the dotted lines in FIG. 6A was obtained when $^{15}$N-arginine was omitted from the injection solution. In addition, when $^{15}$N-arginine was administered at a level of 5 mg/mouse, the signal intensity of the [(MGD)$_2$/Fe—$^{15}$NO] complex was reduced compared to that of the [(MGD)$_2$/Fe—$^{14}$NO] complex (FIG. 6B). The results clearly confirm that the NO detected in the LPS-treated mouse urine was overproduced via the arginine-NO synthase pathway.

In summary, the isotopic tracer experiments using $^{15}$N-arginine have unambiguously demonstrated that the NO trapped by the [(MGD)$_2$/Fe] complex either in normal or the LPS-treated mice is produced via arginine-NO pathway (see FIG. 2A, FIG. 2B, FIG. 3A, FIG. 3B, FIG. 4A, FIG. 4B, FIG. 6A and FIG. 6B). The authenticity of NO produced in vivo which is trapped by the [(MGD)$_2$/Fe] complex in our experimental systems is therefore firmly established.

The time-dependent increase in [(MGD)$_2$/Fe—NO] levels detected in urine samples after LPS administration is shown in Table 2.

TABLE 2

Time-dependent changes in the amounts of [(MGD)$_2$/Fe-NO] present in the LPS-treated mouse urine

| Conditions | [(MGD$_2$/Fe-NO] |
|---|---|
| LPSa-treated[b] | |
| 0 h | 1.4 ± 0.4 (3)[c] |
| 2 h | 7.3 ± 2.2 (3)* |
| 4 h | 18.2 ± 4.8 (4)* |
| 6 h | 17.1 ± 4.8 (4)* |
| 8 h | 35.1 ± 5.7 (3)* |
| LPS-treated (after 6 h)[d] | |
| +NMMA (50 mg/kg) | 3.6 ± 0.9 (4)† |
| +NMMA (100 mg/kg) | 7.3 ± 2.2 (3)† |

The amounts of the [(MGD)$_2$/Fe] in mouse urine were determined as described in Table 1. At different times points after LPS challenge as indicated, the mice were injected subcutaneously with [(MGD)$_2$/Fe-NO], and were sacrificed 2 h later to collect urine for EPR measurement.
[c]The data presented are mean S.E. (number of mice).
Various amounts on NMMA were injected intraperitoneally at 6 h after LPS challenge just prior to injection of [(MGD)$_2$/Fe]. Urine was collected 2 h later.
*$P < 0.05$ compared with controls (see Table 1).
†$P < 0.05$ compared with the LPS-treated group at 6 h.

EXAMPLE 7

In Vivo Reduction of—NO Levels by [(MGD)$_2$/Fe] Complex in LPS-treated Mice The time-dependent increase in plasma nitrate levels in LPS-treated mice was determined as previously described (see Komarov and Lai, supra). The results are summarized in Table 3.

TABLE 3

Effects of LPS and [(MGD)$_2$/Fe] on total nitrate/nitrite levels in mouse plasma

| Conditions | Nitrate/Nitrite, μM[a] |
|---|---|
| Controls | 73 ± 7 (10)d |
| LPS-treated[b] | |
| 2 h | 103 ± 10 (6)* |
| 4 h | 291 ± 38 (6)* |
| 6 h | 506 ± 75 (4)* |
| 8 h | 638 ± 29 (8)* |
| LPS + [MGD)$_2$/Fe] complex[c] | |
| 8 h | 336 ± 46 (3)*† |

The nitrate/nitrite determination in the mouse plasma was performed as previously described (see Komarov and Lai, supra).
The mice were sacrificed at different time points as indicated after intravenous injection of LPS.
At 6 h after LPS challenge the mice were injected subcutaneously with [(MGD)$_2$/Fe] and were sacrificed 2 h later.
The data presented are mean S.E. (number of mice).
*$P < 0.05$ compared with controls.
†$P < 0.05$ compared with the LPS-treated group at 8 h.

Nitrate levels are seen to increase with time after LPS challenge. Injection of the NO trapping agent, [(MGD)$_2$/Fe], reduced the nitrate level in the plasma by about one-half, a result suggesting that the trapping of NO by [(MGD)$_2$/Fe] in the LPS-treated mice prevents it from interaction with hemoglobin in the red blood cells, thereby reducing nitrate levels in the plasma. These results demonstrate that the administration of a nitric oxide scavenger, such as the [(MGD)$_2$/Fe] complex, is effective to reduce in vivo NO levels in LPS-treated mice.

EXAMPLE 8

Although the route by which the subcutaneously injected spin-trapping reagent enters the tissues before its excretion into the urine is not yet known, it can be speculated that upon subcutaneous injection, the [(MGD)$_2$/Fe] complex diffuses across the capillary bed, where it interacts with NO produced by. NO synthases to form the [(MGD)$_2$/Fe—NO] complex. The latter complex then enters the blood circulation and is eventually excreted and concentrated in the urine, thereby reducing in vivo NO levels. The isolated urine containing the [(MGD)$_2$/Fe—NO] complex was found to be stable at 4C for several hours. When the [(MGD)$_2$/Fe] complex was injected intravenously into normal or LPS-treated mice, the EPR signal of the [(MGD)$_2$/Fe—NO] complex was also detected in the urine. This suggests that regardless of the route of administration employed, nitric oxide scavengers, such as the [(MGD)$_2$/Fe] complex, are capable of interacting with the NO produced in vivo to form an NO-containing complex, which reduces in vivo NO levels.

EXAMPLE 9

As shown in Example 7, subcutaneous administration of the [(MGD)$_2$/Fe] complex reduced the in vivo NO levels in LPS-treated mice. Since excessive NO production is known to induce systemic hypotension, injections of the [(MGD)$_2$/Fe] complex that reduce in vivo NO levels should also restore blood pressure in hypotensive animals induced by LPS treatment. To test this idea, experiments were carried out to determine the effects of administration of the [(MGD)$_2$/Fe] complex on the blood pressure of the hypotensive rats induced by LPS challenge.

Thus, male Wistar rats (230–300 g) fasted overnight were anesthetized with thiobutabarbital (Inactin, 100 mg/kg, i.p.). A catheter was implanted in the femoral vein for drug infusions. The femoral artery was cannulated for continuous blood pressure measurement. Rats were injected with an i.v. bolus dose of LPS (S.Typhosa endotoxin, 4 mg/kg). Two hours after LPS challenge, rats were then subjected to one of the following treatments:

(a) Control, saline infusion- 1.0 ml saline i.v. injection followed by 1.0 ml/hr of saline infusion for 1.5 hours, (b) [(MGD)$_2$/Fe] (at a ratio of 2-to-0.4)-0.1 mmole/kg i.v. bolus injection followed by 0.1 mmole/kg infusion for 1.5 hours, (c) [(MGD)$_2$/Fe] (at a ratio of 2-to-0.2)-0.1 mmole/kg i.v. bolus injection followed by 0.1 mmole/kg infusion for 1.5 hours, and (d) [(MGD)$_2$/Fe] (at a ratio of 2-to-0)-0.1 mmole/kg i.v. bolus injection followed by 0.1 mmole/kg infusion for 1.5 hours. The results of mean arterial pressure (MAP) measurement are summarized in Table 4.

TABLE 4

Effects of various ratios of [(MGD)$_2$/Fe] treatment on the mean arterial pressure (MAP in mmHg) in the lipopolysaccharide (LPS)-induced shocked rats.

| Conditions[1] | Baseline[2] (meanSEM) | 2 hrs after LPS Treatment | 1.5 hrs after Treatment |
|---|---|---|---|
| a) Control saline (n = 16)[3] | 96 ± 2 | 77 ± 2 | 78 ± 4 |

TABLE 4-continued

Effects of various ratios of [(MGD)₂/Fe] treatment on the mean arterial pressure (MAP in mmHg) in the lipopolysaccharide (LPS)-induced shocked rats.

| Conditions[1] | Baseline[2] (meanSEM) | 2 hrs after LPS Treatment | 1.5 hrs after Treatment |
|---|---|---|---|
| b) [(MGD)₂/Fe] (2/0.4)[4] (n = 16) | 95 ± 3 | 75 ± 2 | 96 ± 3 |
| c) [(MGD)₂/Fe] (2/0.2) (n = 6) | 98 ± 3 | 73 ± 4 | 87 ± 4 |
| d) MGD (2/0) (n = 6) | 102 ± 5 | 73 ± 2 | 94 ± 6 |

1. Experimental conditions were as described in the text.
2. The values of MAP prior to LPS treatment.
3. n, the number of animals in each group.
4. [(MGD)₂/Fe] (2/0.4) is defined as the ratio of [(MGD)₂/Fe] to be 2-to-0.4.

The MAP of anesthetized rats was in the range of 96 to 102 mmHg. Two hours after LPS treatment, the MAP decreased to between 73 and 77 mmHg, which is indicative of the onset of systemic hypotension, caused by abnormally elevated levels of nitric oxide. While the 1.5 hr saline infusion did not change the MAP, infusions of [(MGD)₂/Fe] complex at various ratios, ranging from 2-to-0.4 (MGD to Fe) to 2-to-0 (MGD to Fe), restored the blood pressure to 87–96 mmHg (Table 4). These results suggest that the i.v. infusion of MGD either with or without added iron (Fe) can restore normal blood pressure in hypotensive rats induced by LPS challenge (Table 4).

Since MGD does not bind NO, it is speculated that the restoration of the MAP by MGD infusion may at least in part be attributed to the MGD chelation of cellular iron released by excess NO production, which is known to attack cellular iron-containing proteins and result in cellular iron loss during sepsis or septic shock. This example shows that MGD, either with or without added iron, is effective for the treatment of systemic hypotension, a condition which is associated with many inflammatory and/or infectious diseases.

While the invention has been described in detail with reference to certain preferred embodiments thereof, it will be understood that modifications and variations are within the spirit and scope of that which is described and claimed.

What is claimed is:

1. A method for treating free radical overproduction in a subject in need thereof, said method comprising administering to said subject an effective amount of at least one physiologically compatible dithiocarbamate-containing free radical scavenger, wherein said dithiocarbamate-containing free radical scavenger has the structure I or II as follows:

$$[R_1R_2N-C(S)-S]_xM^{+1, +2, +3} \quad (I)$$

wherein:

each of $R_1$ and $R_2$ is independently selected from a $C_1$ up to $C_{18}$ allyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, or substituted arylalkyl, x is 1 or 2, and M is a monovalent cation when x is 1, or M is a physiologically compatible divalent or trivalent transition metal cation when x is 2 or 3, or

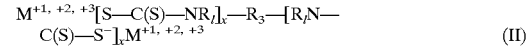

wherein:

each of $R_1$ is independently selected from a $C_1$ up to $C_{18}$ alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, or substituted arylalkyl, $R_3$ is a divalent moiety selected from alkylene, substituted alkylene, oxyalkylene, substituted oxyalkylene, alkenylene, substituted alkenylene, arylene, substituted arylene, alkarylene, substituted alkarylene, aralkylene, or substituted aralkylene, x is 1 or 2, and M is a monovalent cation when x is 1, or M is a physiologically compatible divalent or trivalent transition metal cation when x is 2 or 3.

2. A method according to claim 1 wherein said free radical overproduction is associated with aging, septic shock, ischemia, administration of cytokines, overexpression of cytokines, ulcer, inflammatory bowel disease, gastritis, ulcerative colitis, Crohn's disease, diabetes, arthritis, asthma, Alzheimer's disease, Parkinson's disease, multiple sclerosis, cirrhosis, allograft rejection, transplant rejection, encephalomyelitis, meningitis, pancreatitis, peritonitis, vasculitis, lymphocytic choriomeningitis, glomerulonephritis, opthalmologic diseases, uveitis, glaucoma, blepharitis, chalazion, allergic eye disease, corneal ulcer, keratitis, cataract, retinal disorder, age-related macular degeneration, optic neuritis, ileitis, inflammation induced by overproduction of inflammatory cytokines, liver inflammation, renal inflammation, airway inflammation, hemorrhagic shock, anaphylactic shock, burn, infection leading to overproduction of inflammatory cytokines, hemodialysis, chronic fatigue syndrome, stroke, cancer, cardiovascular diseases associated with overproduction of inflammatory cytokines, ischemic/reperfusion injury associated with overproduction of inflammatory cytokines, toxic shock syndrome, adult respiratory distress syndrome, cachexia, myocarditis, autoimmune disorders, eczema, psoriasis, heart failure, dermatitis, urticaria, cerebral ischemia, systemic lupus erythematosis, AIDS, AIDS dementia, neurodegenerative disorders, chronic neurodegenerative disease, chronic pain, priapism, cystic fibrosis, amyotropic lateral sclerosis, schizophrenia, depression, premenstrual syndrome, anxiety, addiction, migraine, Huntington's disease, epilepsy, gastrointestinal motility disorders, obesity, hyperphagia, solid tumors, malaria, hematologic cancers, myelofibrosis, lung injury, graft-versus-host disease, head injury, CNS trauma, hepatitis, renal failure, liver disease, drug-induced lung injury, transplant rejection and/or preservation, fertility enhancement, bacterial translocation, circulatory shock, traumatic shock, vascular aneurysm, lack of immune response to vaccination, ileus, myocardial infarction, cerebral vasospasms, hearing loss or organ preservation.

3. A method according to claim 1 wherein said free radical overproduction is associated with septic shock.

4. A method according to claim 1 wherein said free radical overproduction is associated with inflammatory bowel disease.

5. A method according. to claim 1 wherein said free radical overproduction is associated with ulcerative colitis.

6. A method according to claim 1 wherein said free radical. overproduction is associated with Crohn's disease.

7. A method according to claim 1 wherein said free radical overproduction is associated with diabetes.

8. A method according to claim 1. wherein said free radical overproduction is associated with asthma.

9. A method according to claim 1 wherein said free radical overproduction is associated with Alzheimer's disease.

10. A method according to claim 1 wherein said free radical overproduction is associated with Parkinson's disease.

11. A method according to claim 1 wherein said free radical overproduction is associated with multiple sclerosis.

12. A method according to claim 1 wherein said free radical overproduction is associated with transplant rejection.

13. A method according to claim 1 wherein said free radical overproduction is associated with hemorrhagic shock.

14. A method according to claim 1 wherein said free radical overproduction is associated with stroke.

15. A method according to claim 1 wherein said free radical overproduction is associated with cancer.

16. A method according to claim 1 wherein said free radical overproduction is associated with systemic lupus.

17. A method according to claim 1 wherein said free radical overproduction is associated with erythematosis.

18. A method according to claim 1 wherein said free radical overproduction is associated with AIDS.

19. A method according to claim 1 wherein said free radical overproduction is associated with neurodegenerative disorders.

20. A method according to claim 1 wherein said free radical overproduction is associated with migraine.

21. A method according to claim 1 wherein said free radical overproduction is associated with obesity.

22. A method according to claim 1 wherein said free radical overproduction is associated with circulatory shock.

23. A method according to claim 2 wherein said cytokine is IL-1, IL-2, IL-6, IL-12, tumor necrosis factor, or interferon-gamma.

24. A method according to claim 2 wherein said free radical overproduction is associated with infection leading to overproduction of inflammatory cytokines.

25. A method according to claim 24 wherein said infection is a bacterial infection.

26. A method according to claim 24 wherein said infection is a viral infection.

27. A method according to claim 24 wherein said infection is a fungal infection.

28. A method according to claim 24 wherein said infection is a parasitic infection.

29. A method according to claim 2 wherein said free radical overproduction is associated with cardiovascular diseases associated with overproduction of inflammatory cytokines.

30. A method according to claim 29 wherein said cardiovascular disease is heart disease.

31. A method according to claim 29 wherein said cardiovascular disease is cardiopulmonary bypass.

32. A method according to claim 29 wherein said cardiovascular disease is ischemic/reperfusion injury.

33. A method according to claim 2 wherein said free radical overproduction is associated with vascular aneurysm.

34. A method according to claim 33 wherein said vascular aneurysm is an aortic aneurysm.

35. A method according to claim 1 wherein said free radical scavenger has the structure (III) as follows:

(III)

wherein each of $R_1$ and $R_2$ is independently selected from a $C_1$ up to $C_{18}$ alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, or $R_1$ or $R_2$ is a divalent moiety selected from the group consisting of alkylene, substituted alkylene, oxyalkylene, substituted oxyalkylene, alkenylene, substituted alkenylene, arylene, substituted arylene, alkarylene, substituted alkarylene, aralkylene and substituted aralkylene, wherein said divalent moiety serves as the same substituent for two dithiocarbamate structures, thereby linking said structures together so as to form a bis(dithiocarbamate) species, and M is Fe.

36. A method for the in vivo reduction of free radical levels in a subject, said method comprising administering to said subject an effective amount of at least one physiologically compatible dithiocarbamate-containing free radical scavenger, wherein said dithiocarbamate-containing fee radical scavenger has the structure I or II as follows:

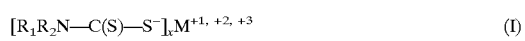

(I)

wherein:

each of $R_1$ and $R_2$ is independently selected from a $C_1$ up to $C_{18}$ allyl, substituted alkyl, cycloalkyl, substituted cycloalkyl, alkenyl, substituted alkenyl, alkynyl, substituted alkynyl, aryl, substituted aryl alkylaryl, substituted alkylaryl arylalkyl, or substituted arylalkyl, x is 1 or 2, and M is a monovalent cation when x is 1, or M is a physiologically compatible divalent or trivalent transition metal cation when x is 2 or 3, or

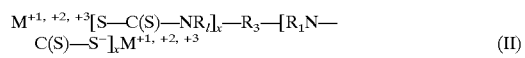

(II)

wherein;

each of $R_1$ is independently selected from a $C_1$ up to $C_{18}$ alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, or substituted arylalkyl, $R_3$ is a divalent moiety selected from alkylene, substituted alkylene, oxyalkylene, substituted oxyalkylene, alkenylene, substituted alkenylene, arylene, substituted arylene, alkarylene, substituted alkarylene, aralkylene, or substituted aralkylene, x is 1 or 2, and M is a monovalent cation when x is 1, or M is a physiologically compatible divalent or trivalent transition metal cation when x is 2 or 3.

37. A method for treating free radical overproduction in a subject in need thereof, said method comprising administering to said subject an effective amount of at least one physiologically compatible compound which noncovalently binds free radicals, wherein said compound has the structure I or II as follows:

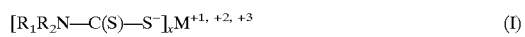

(I)

wherein:

each of $R_1$ and $R_2$ is independently selected from a $C_1$ up to $C_{18}$ alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, or substituted arylalkyl, x 1 or 2, and M is a monovalent cation when x is 1, or M is a physiologically compatible divalent or trivalent transition metal cation when x is 2 or 3, or

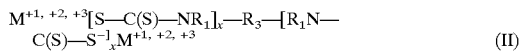

(II)

wherein:
each of $R_1$ is independently selected from a $C_1$ up to $C_{18}$ alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, or substituted arylalkyl, $R_3$ is a divalent moiety selected from alkylene, substituted alkylene, oxyalkylene, substituted oxyalkylene, alkenylene, substituted alkenylene, arylene, substituted arylene, alkarylene, substituted alkarylene, aralkylene, or substituted aralkylene, x is 1 or 2, and M is a monovalent cation when x is 1, or M is a physiologically compatible divalent or trivalent transition metal cation when x is 2 or 3.

38. A method for the in vivo reduction of free radical levels in a subject, said method comprising administering to said subject an effective amount of at least one physiologically compatible compound which non-covalently binds free radicals, wherein said compound has the structure I or II as follows:

$$[R_1R_2N\text{---}C(S)\text{---}S^-]_xM^{+1, +2, +3} \quad (I)$$

wherein:
each of $R_1$ and $R_2$ is independently selected from a $C_1$ up to $C_{18}$ alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, or substituted arylalkyl, x is 1 or 2, and M is a monovalent cation when x is 1, or M is a physiologically compatible divalent or trivalent transition metal cation when x is 2 or 3, or

(II)

wherein:
each of $R_1$ is independently selected from a $C_1$ up to $C_{18}$ alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, or substituted arylalkyl, $R_3$ is a divalent moiety selected from alkylene, substituted alkylene, oxyalkylene, substituted oxyalkylene, alkenylene, substituted alkenylene, arylene, substituted arylene, alkarylene, substituted alkarylene, aralkylene, or substituted aralkylene, x is 1 or 2, and M is a monovalent cation when x is 1, or M is a physiologically compatible divalent or trivalent transition metal cation when x is 2 or 3.

39. A method for treating free radical overproduction in a subject in need thereof, said method comprising administering to said subject an effective amount of at least one spin trapping agent which non-covalently binds free radicals, wherein said agent has the structure I or II as follows:

$$[R_1R_2N\text{---}C(S)\text{---}S^-]_xM^{+1, +2, +3} \quad (I)$$

wherein:
each of $R_1$ and $R_2$ is independently selected from a $C_1$ up to $C_{18}$ alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, or substituted arylalkyl, x is 1 or 2, and M is a monovalent cation when x is 1, or M is a physiologically compatible divalent or trivalent transition metal cation when x is 2 or 3, or

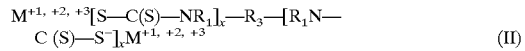

(II)

wherein:
each of $R_1$ is independently selected from a $C_1$ up to $C_{18}$ alkyl, substituted alkyl, cycloalkyl, substituted cycloalkyl alkenyl, substituted alkenyl, alkynyl, substituted alkynyl, aryl, substituted aryl, alkylaryl, substituted alkylaryl, arylalkyl, or substituted arylalkyl, $R_3$ is a divalent moiety selected from alkylene, substituted alkylene, oxyalkylene, substituted oxyalkylene, alkenylene, substituted alkenylene, arylene, substituted arylene, alkarylene, substituted alkarylene, aralkylene, or substituted aralkylene, x is 1 or 2, and M is a monovalent cation when x is 1, or M is a physiologically compatible divalent or trivalent transition metal cation when x is 2 or 3.

40. A method for the in vivo reduction of free radical levels in a subject, said method comprising administering to said subject an effective amount of at least one spin trapping agent which non-covalently binds free radicals, wherein said agent has the structure I or II as follows:

$$[R_1R_2N\text{---}C(S)\text{---}S^-]_xM{+1, +2, +3} \quad (I)$$

wherein:
each of $R_1$ and $R_2$ is independently selected from a $C_1$ up to $C_{18}$ alkyl, substituted alkyl, cycloalkyl, substituted cycloalkyl, alkenyl, substituted alkenyl, alkynyl, substituted alkynyl, aryl, substituted aryl, alkylaryl substituted alkylaryl, arylalkyl, or substituted arylalkyl, x is 1 or 2, and M is a monovalent cation when x is 1, or M is a physiologically compatible divalent or trivalent transition metal cation when x is 2 or 3, or

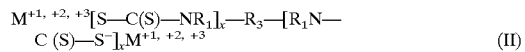

(II)

wherein:
each of $R_1$ is independently selected from a $C_1$ up to $C_{18}$ alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, or substituted arylalkyl, $R_3$ is a divalent moiety selected from alkylene, substituted alkylene, oxyalkylene, substituted oxyalkylene, alkenylene, substituted alkenylene, arylene, substituted arylene, alkarylene, substituted alkarylene, aralkylene, or substituted aralkylene, x is 1 or 2, and M is a monovalent cation when x is 1, or M is a physiologically compatible divalent or trivalent transition metal cation when x is 2 or 3.

41. A method according to claim 1 wherein said free radical scavenger is delivered orally, intravenously, subcutaneously, parenterally, topically, rectally or by inhalation.

42. A method according to claim 1 wherein said free radical scavenger is delivered in the form of a solid, solution, emulsion, dispersion, micelle or liposome.

* * * * *

UNITED STATES PATENT AND TRADEMARK OFFICE
CERTIFICATE OF CORRECTION

PATENT NO. : 6,469,057 B1  Page 1 of 1
DATED : October 22, 2002
INVENTOR(S) : Ching-San Lai It is certified that error appears in the above-identified patent and that said Letters Patent is hereby corrected as shown below:

Column 19,
Line 59, change "allyl" to -- alkyl --; and

Column 22,
Line 22, change "allyl" to -- alkyl --.

Signed and Sealed this

Eighth Day of April, 2003

JAMES E. ROGAN
*Director of the United States Patent and Trademark Office*